United States Patent
Stauber et al.

(10) Patent No.: US 10,132,796 B2
(45) Date of Patent: Nov. 20, 2018

(54) METHOD FOR DETECTING AND QUANTIFYING A TARGET MOLECULE IN A TISSUE

(75) Inventors: Jonathan Stauber, Lille (FR); David Bonnel, Laventie (FR)

(73) Assignee: IMABIOTECH, Loos (FR)

( * ) Notice: Subject to any disclaimer, the term of this patent is extended or adjusted under 35 U.S.C. 154(b) by 247 days.

(21) Appl. No.: 14/123,128

(22) PCT Filed: May 29, 2012

(86) PCT No.: PCT/FR2012/051205
§ 371 (c)(1),
(2), (4) Date: Nov. 29, 2013

(87) PCT Pub. No.: WO2012/164221
PCT Pub. Date: Dec. 6, 2012

(65) Prior Publication Data
US 2014/0106391 A1    Apr. 17, 2014

(30) Foreign Application Priority Data
May 31, 2011    (FR) ..................... 11 54731

(51) Int. Cl.
| | |
|---|---|
| G01N 33/48 | (2006.01) |
| G01N 33/50 | (2006.01) |
| G01N 33/68 | (2006.01) |
| G01N 1/38 | (2006.01) |
| G01N 33/483 | (2006.01) |
| G06G 7/58 | (2006.01) |
| G01N 1/28 | (2006.01) |

(52) U.S. Cl.
CPC .......... *G01N 33/5091* (2013.01); *G01N 1/38* (2013.01); *G01N 33/4833* (2013.01); *G01N 33/6851* (2013.01); *G01N 2001/2866* (2013.01); *G01N 2001/2893* (2013.01)

(58) Field of Classification Search
CPC ......................................... G01N 19/20–19/28
See application file for complete search history.

(56) References Cited

U.S. PATENT DOCUMENTS

| | | |
|---|---|---|
| 2012/0258485 A1 | 10/2012 | Stauber et al. |
| 2015/0377862 A1 | 12/2015 | Hamm et al. |
| 2016/0003836 A1 | 1/2016 | Stauber et al. |

FOREIGN PATENT DOCUMENTS

| | | |
|---|---|---|
| EP | 1 580 682 | 9/2005 |
| EP | 2 163 900 | 3/2010 |
| FR | 2 973 112 | 9/2012 |
| WO | WO 2007/000669 | 1/2007 |
| WO | WO 2011/073740 | 6/2011 |
| WO | WO 2014/125112 | 8/2014 |
| WO | WO 2014/128309 | 8/2014 |

OTHER PUBLICATIONS

Becker, J. Sa. et al. "Elemental imaging mass spectrometry of thin sections of tissues and analysis of brain proteins in gels by laser ablation inductively coupled plasma mass spectrometry" *Physica Status Solidi (C)*, May 1, 2007, pp. 1775-1784, vol. 4., No. 6.
Hare, D. et al. "Quantitative elemental bio-imaging of Mn, Fe, Cu, and Zn in 6-hydroxydopamine induced Parkinsonism mouse models" *Metallomics*, Jan. 1, 2009, pp. 53-58, vol. 1, No. 1.
Kaletas, B. K. et al. "Sample preparation issues for tissue imaging by imaging MS" *Proteomics*, May 1, 2009, pp. 2622-2633, vol. 9, No. 10.
Drexler, D. M. et al. "Utility of imaging mass spectrometry (IMS) by matrix-assisted laser desorption ionization (MALDI) on an ion trap mass spectrometer in the analysis of drugs and metabolites in biological tissues" *Journal of Pharmacological and Toxicological Methods*, May 1, 2007, pp. 279-288, vol. 55, No. 3.
Notari, S. et al. "Determination of anti-HIV drug concentration in human plasma by MALDI-TOF/TOF" *Journal of Chromatography B.*, Mar. 20, 2006, pp. 109-116 vol. 833, No. 1.
Hare, D. J. et al. "Three-dimensional elemental bio-imaging of Fe, Zn, Cu, Mn and P in a 6-hydroxydopamine lesioned mouse brain" *Metallomics*, Jan. 1, 2010, pp. 745-753, vol. 2, No. 11.
Zabet-Moghaddam, M. et al. "Qualitative and quantitative analysis of low molecular weight compounds by ultraviolet matrix-assisted laser desorption/ionization mass spectrometry using ionic liquid matrices" *Rapid Communications in Mass Spectrometry*, 2004, pp. 141-148, vol. 18.
Written Opinion in International Application No. PCT/FR2012/051205, dated Aug. 6, 2012, pp. 1-8.
Hamm, G. et al. "Quantitative mass spectrometry imaging of propranolol and olanzapine using tissue extinction calculation as normalization factor" *Journal of Proteomics*, 2012, pp. 4952-4961.
Tech Tip #6 Thermoscientific, "Extinction coefficients" 2008, pp. 1-3.
Stauber, J. "Quantitation by MS imaging: needs and challenges in pharmaceuticals" *Bioanalysis*, Sep. 2012, vol. 4, No. 17, pp. 2095-2098.
Sugiura, Y. et al. "Imaging Mass Spectrometry for Visualization of Drug and Endogenous Metabolite Distribution: Toward in Situ Pharmacometabolomes" *Journal of Neuroimmune Pharmacology*, Mar. 1, 2010, vol. 5, No. 1, pp. 31-43.
Written Opinion in International Application No. PCT/EP2014/053654, dated Jul. 28, 2014, pp. 1-5.
Lemaire, R. et al. "Tag-Mass: Specific Molecular Imaging of Transcriptome and Proteome by Mass Spectrometry Based on Photocleavable Tag" *Journal of Proteome Research*, Jun. 1, 2007, vol. 6, No. 6, pp. 2057-2067.
Stauber, J. et al. "Specific MALDI-MSI: TAG-MASS" In Mass Spectrometry Imaging: Principles and Protocols, Humana Press, Jan. 1, 2010, pp. 339-361.
Written Opinion in International Application No. PCT/EP2014/053047, dated Apr. 16, 2014, pp. 1-6.

*Primary Examiner* — Eric S Dejong
(74) *Attorney, Agent, or Firm* — Saliwanchik, Lloyd & Eisenschenk (57) ABSTRACT

The invention relates to a method for preparing a dilution range of at least one standard molecule for a tissue, whereby a tissue homogenate is used, to which the standard molecule is added, the resulting mixture being conditioned and sliced before the analysis of a slice of said tissue. The invention also relates to a method for detecting and quantifying at least one target molecule in at least one tissue using a standard range according to the invention.

16 Claims, 2 Drawing Sheets

METHOD FOR DETECTING AND QUANTIFYING A TARGET MOLECULE IN A TISSUE

CROSS-REFERENCE TO RELATED APPLICATION

This application is the U.S. national stage application of International Patent Application No. PCT/FR2012/051205, filed May 29, 2012.

FIELD OF THE INVENTION

The invention relates to the preparation of a dilution range of a molecule for a tissue and the use of such a dilution range for the quantification of said molecule in said tissue, for example by mass spectrometry. The dilution range according to the invention takes account of the specific behaviour of the molecule to be quantified in the tissue of interest. More particularly, the invention provides a method making it possible to detect and/or quantify a target molecule directly on the surface of a tissue by using mass spectrometry imaging, and notably MALDI imaging. The invention also relates to a method for validating a detection and/or quantification method, as well as a method for controlling the quality and/or the reproducibility of a detection and/or quantification method.

Generally, the invention is applicable throughout the field in which the detection and/or the quantification of a molecule in a tissue is useful/necessary. The invention is, for example, applicable in the pharmaceutical field for studying the distribution and the pharmacokinetics of a medicine in different biological tissues. Similarly, the invention is applicable in the biomedical field, for example for detecting, identifying and tracing a given biomarker in a pathological tissue at a given instant. The invention is also applicable in the field of agriculture chemistry, for example for evaluating the toxicity and the degradation of a molecule such as a phytosanitary product in plants.

STATE OF THE ART

Various techniques are currently used to detect and identify a molecule in a sample, notably a tissue. For example, mass spectrometry is a technique that is widely known and used in chemical and biochemical analysis for detecting and identifying molecules of interest in a sample. For some years now, molecular imaging by mass spectrometry, such as MALDI imaging, has been developing, making it possible to visualize the distribution of molecules of interest directly on slices of biological tissues. MALDI imaging, because of its very high sensitivity, makes it possible to simultaneously visualize the distribution of a very large number of different molecules directly on the surface of the tissues. In the pharmaceutical field, this technology makes it possible, for example, to compare the distribution of a molecule in different organs at different treatment times.

However, in the case where a quantification of the molecule thus detected at the instant t is desired, this imaging technique has to be coupled with a quantitative chemical analysis, based on a conventional or instrumental method. This second quantification step is a source of manipulation and interpretation errors. Furthermore, it does not allow for a direct correlation between the presence of the molecule of interest and its quantitative distribution in the tissue.

Moreover, a given molecule in a given concentration does not emit a signal of the same intensity according to the tissue in which it is detected. Similarly, two different molecules in an identical concentration in a given tissue exhibit a different signal intensity.

This phenomenon can be explained by the existence of a tissue extinction coefficient (TEC), or tissue effect, or even ion suppression effect, specific to each molecule and each tissue. The TEC is representative of the loss or gain in intensity of the signal from a given molecule according to the tissue and/or its location in the tissue, relative to the signal from said molecule on an inert analysis support. The TEC is dependent on a number of factors, notably the nature of the tissue (animal or plant), the chemical environment, the chemical treatment or not of the tissue, etc. The existence of this TEC makes it difficult to interpret the intensity of the signal emitted by a molecule in a tissue during an analysis, notably in mass spectrometry.

SUMMARY OF THE INVENTION

The invention proposes a method that makes it possible to prepare a dilution range, or standard range, of a given molecule for a given tissue. The standard range according to the invention is prepared by using a slice of a reconstitution of the tissue of interest from a fragmented tissue. The inventors have discovered that a given molecule behaves in an equivalent manner in such a reconstituted tissue and in the corresponding whole tissue. In the case of an analysis by mass spectrometry, the mass spectrum of the molecule in the reconstituted tissue is substantially identical to the mass spectrum of the same molecule, in the same concentration, in the corresponding whole tissue. Similarly, in the case of an analysis by fluorescence, the intensity of the fluorescent signal emitted by the labeled molecule in the reconstituted tissue is substantially identical to the intensity of the fluorescent signal emitted by the same labeled molecule, in the same concentration, in the corresponding whole tissue. Also, by using a standard range according to the invention for a quantitative analysis of a given molecule in a given tissue, there is no need to take account of the TEC. The signal obtained in the analysis of said molecule in said tissue can be directly correlated with the signals of the corresponding standard range.

The invention also proposes a method for detecting and/or quantifying a target molecule in a tissue, regardless of the detection method and notably by ionization, radioactivity or fluorescence. For example, the method according to the invention uses mass spectrometry, or mass spectrometry imaging, allowing for an automated acquisition of a signal linked to the mass spectrum of the molecule, directly on a slice of the tissue, in order to reconstruct images of the distribution and of the quantity of said target molecule in the tissue. For this, according to the invention, a dilution range of the target molecule, or of a molecule exhibiting similar physical-chemical characteristics, is used, produced by using a slice of a reconstituted tissue from a tissue identical to the tissue to be analysed. An accurate quantification of the molecule in the tissue is then possible by direct comparison with the results from the dilution range.

The invention also proposes a method for validating a method for detecting and/or quantifying a target molecule in a tissue by using a slice of tissue. The validation method according to the invention makes it possible to check, for a given tissue and a given molecule, that the analysis results obtained for said molecule directly on a slice of said tissue will be representative of said tissue, independently of the tissue effect.

The invention also proposes a method for controlling the quality and/or the reproducibility of a method for detecting and/or quantifying a target molecule in a tissue by using a slice of tissue. Such a method makes it possible to track the experimental variabilities and/or take them into account, notably by normalizing the values obtained for each analysis relative to this quality control in order, for example, to relatively quantify compound(s) of interest between different analyses.

The subject of the invention is therefore a method for preparing a dilution range of at least one standard molecule for a tissue, comprising the steps consisting of:

(i) grinding a tissue to obtain a tissue homogenate;

(ii) mixing the standard molecule with a first sample of the tissue homogenate from the step (i), said standard molecule being in a first known concentration;

(iii) conditioning the first sample of tissue homogenate obtained from the step (ii) so as to be able to slice said conditioned sample of tissue homogenate;

(iv) repeating the steps (ii) and (iii) with at least one second sample of the tissue homogenate from the step (i) and a second known concentration of the standard molecule, different from the first concentration; and (v) analysing at least one slice of each of the conditioned samples of tissue homogenate obtained from the step (iii), so as to obtain a signal representative of the quantity of standard molecule in the tissue for each of the concentrations of said standard molecule.

The method according to the invention can be applied to any biological tissue, whether animal or plant. A "tissue" should be understood generally to be an assembly of cells of the same origin and grouped together in a functional assembly to contribute to the same function. In certain cases, a tissue can be understood to be an organ or a part of an organ.

The standard molecule can be a peptide, a polypeptide, a protein, an amino acid, a nucleic acid, a lipid, a metabolite, a small molecule such as a drug, etc. More generally, the standard molecule can be any pharmaceutically, biologically or otherwise active molecule. Depending on the analysis that has to be performed in the step (v), the standard molecule can be non-labeled or labeled, and notably radio-labeled or labeled with a fluorescent molecule, such as GFP (Green Fluorescent Protein).

In the grinding step (i), the tissue can be fragmented so as to form a more or less fine homogenate, notably liquid, semi-liquid, pasty, etc. The tissue homogenate may not be homogeneous and may for example include tissue fragments of different sizes. It is possible, if necessary, to add a homogenizing solution to the homogenate obtained, and notably an aqueous solution, so as to dilute said homogenate and render it less compact. The homogenizing solution can be added upstream, downstream or during the grinding step.

The grinding can be done by any means, notably manual or mechanical. For example, the tissue homogenate can be obtained by shearing using a blender, or by crushing using a pestle.

According to the invention, the tissue used in the step (i) is advantageously an organ, such as a kidney, a liver, etc. A whole organ or just a portion of said organ can be used without distinction to produce the standard range. The tissue can be ground before being subdivided into at least as many samples of tissue homogenate as there are dilution points in the standard range to be produced. It is also possible to proceed with the dividing up of said tissue before the grinding, each sample being individually ground. It is also possible to use one or more different organs, whole or not, for each of the dilution points of the standard range, the organs used for the production of one and the same series being of identical nature and origin each time. For example, for the production of a standard range of a molecule in a rat liver, comprising four dilution points, or concentrations, a new rat liver is used for each concentration.

Preparations of the standard molecule in at least two different concentrations are produced. For example, the standard molecule is placed in suspension in a solubilization solution (aqueous or containing a solvent) at different known concentrations. The same amount of solution is then added to each of the samples of tissue homogenate, each having a different and known concentration of said standard molecule. In another example the standard molecule is placed in suspension in a solubilization solution, different quantities of said solution being added to each of the samples of tissue homogenate, so that each sample of tissue homogenate obtained from the step (ii) has a different and known concentration of said standard molecule. Preferentially, the dilution range comprises between 2 and 10 dilution points.

Advantageously, before the conditioning step (iii), a homogenizing step is provided, in order to obtain a uniform distribution of the standard molecule in the sample of tissue homogenate. This homogenizing step can, for example, be done using a mixer such as a vortex.

In an embodiment, the steps (i), (ii) and, where appropriate, the homogenizing step are carried out successively; it is obviously possible to conduct all or part of these steps simultaneously. For example, the tissue is ground with the solution containing the standard molecule.

The conditioning step (iii) consists of processing and/or shaping the sample of tissue homogenate to allow it to be cut in order to obtain at least one slice of said homogenate.

For example, the conditioning comprises a step of freezing the sample of tissue homogenate. For this, the sample of tissue homogenate is, for example, placed in a mould, of any shape, the whole then being frozen by any appropriate technique. For example, said mould is dipped in liquid nitrogen, in order to provoke an instantaneous freezing of all of the mass, then kept at −18° C. until the cutting step.

In another example, the conditioning step consists of coating said sample of tissue homogenate, notably in paraffin, resin or gelatine. Coating should be understood to mean a covering which entirely surrounds the sample of tissue homogenate. The coating step can notably be carried out by using a mould.

Obviously, the freezing step can be followed by a coating step.

The choice of the conditioning may notably depend on the state of the sample of tissue homogenate. For example, if the tissue homogenate obtained from the step (ii) is liquid, it will advantageously be chosen to freeze the sample of tissue homogenate to allow for subsequent cutting. In the case where the homogenate consists of rough-ground tissue, or of a compact paste, a coating in paraffin or similar may allow it to be cut.

In one embodiment, it is possible to use the same mould to condition all or part of the samples of tissue homogenate of the same standard range. In this case, the mould comprises different cells, to allow for a physical separation between the different samples. Advantageously, the partitions delimiting the cells are removable and/or made of a material which can be cut in the same conditions as the samples of tissue homogenate. Thus, it is possible to produce slices from the content of the mould, which each comprise the succession of samples of tissue homogenate of the dilution range being produced. Preferentially, the samples of tissue homogenate are arranged in successive increasing (or decreasing) concentrations in the successive cells.

Once conditioned, the samples of tissue homogenate can, without preference, be maintained in the conditions of conditioning, for example frozen, or be retained in conditions guaranteeing that their integrity is maintained (for example at a temperature of approximately +5° C.), in their moulds or stripped from the moulds, until they are cut and/or used in the analysis step (v).

Advantageously, the sample of tissue homogenate obtained from the step (iii) exhibits a density identical to that of a corresponding whole tissue. Similarly advantageously, the sample of tissue homogenate obtained from the step (iii) exhibits a tissue extinction coefficient (TEC) identical to that of a corresponding whole tissue.

"Density" should be understood to mean the per volume mass of the tissue or of the sample of tissue homogenate.

"Whole tissue" should be understood to mean a tissue identical to the tissue used to produce the samples of tissue homogenate, which retains the inherent qualities/properties of said tissue.

The analysis step (v) is conducted on slices of the samples of tissue homogenate previously produced from conditioned samples of homogenate. Any technology allowing for a molecular analysis of a slice of tissue can be used for the step (v), such as mass spectrometry, analysis by fluorescence, autoradiography, etc.

Generally, a slice is understood to be a section of a tissue (reconstituted or whole). Also, all the slice dimensions compatible with molecular analysis and notably quantitative molecular analysis, for example in a spectrometer or a microscope, can be used. Advantageously, the slices have a thickness of between 2 µm and 50 µm, and notably approximately 20 µm. The thickness is understood to be the dimension extending at right angles to the plane of the slice.

According to examples of implementation of the method of the invention, the slices can be processed before the analysis step. For example, it is possible to proceed with drying of the slice obtained from a sample of tissue homogenate previously frozen or coated. In the case of a slice obtained from a sample of tissue homogenate previously frozen, it is possible to proceed with a cryo-drying of said slice. For example, the slice is placed at −18° C. for a night before the analysis step.

The slices of tissue can be produced from samples of tissue homogenate still frozen, or from said samples once defrosted. Advantageously, for the production of a given dilution range, the same conditioning and possible subsequent treatment(s) are applied to all the samples of tissue homogenate. Preferentially, all the slices used for the production of a given standard range are of substantially identical thickness.

Advantageously, the slices of samples of tissue homogenate are placed on a support, such as a slide, allowing them to be introduced into a spectrometer, a microscope, or similar. Preferentially, all the slices used for the production of a given standard range are arranged on identical supports for the analysis to be conducted.

Generally, the same analysis conditions are advantageously applied to all the samples of tissue homogenate of the same dilution range. Analysis conditions should be understood to mean the settings and parameters applied to the apparatus used for the analysis, and the sample preparation conditions, such as the possible washing steps, the deposition of a matrix in the case of an analysis by spectrophotometry, etc.

Once the signal representative of the quantity of the molecule is obtained for each of the slices of sample of tissue homogenate of the series, it is possible to produce a calibration curve representative of the dilution range.

For example, in the case of an analysis by mass spectrometry, the same signal associated with the mass spectrum of the target molecule will be chosen for all the dilution points, to plot the calibration curve. The signal may notably be the intensity of the peak, the area of the peak or the signal/noise ratio of said mass spectrum.

In the case of an analysis by autoradiography, the intensity of the radioactivity emitted by the standard molecule radio-labeled, for example, with carbon 14 is used. In the case of an analysis by fluorescence, the intensity of the light emission of the standard molecule labeled by a fluorescent molecule is used.

In one embodiment of the method of the invention, at least two different standard ranges are produced at the same time.

For example, at least two different standard molecules are added in the step (ii) to each of the samples of the tissue homogenate, the analysis of the step (v) being conducted for each of the standard molecules so as to obtain the signal representative of the quantity in the standard molecule of each of the standard molecules in the tissue, for each of the concentrations.

Each standard molecule is added to a given sample of tissue homogenate in a given concentration, which may be different from the concentration of the other molecule in said sample of tissue homogenate.

The dilution range according to the invention can be used to compute the smallest quantity of standard molecule that can be detected in the tissue with a given level of confidence, or LOD (Limit of Detection). For this, the smallest signal that can be detected within the limit of detection, that is to say that exhibits a signal/noise value greater than or equal to 3, is identified on the dilution range.

Similarly, the standard range can be used to compute the smallest quantity of standard molecule that can be quantified in the tissue with a given level of confidence, or LOQ (Limit of Quantification). This (signal/noise) value is fixed at international level as having to be equal to three times the LOD value (LOQ=3LOD) and be at least equal to 10.

The dilution range according to the invention can also be used to evaluate the influence of the thickness of the slices and/or of the nature of the matrix and/or of the mode of deposition of said matrix on the detection and/or quantification of the molecule. It is thus possible to determine the optimum slice thickness and/or the most appropriate matrix as a function of the tissue and/or of the molecule.

The dilution range obtained according to the method of the invention can also be used to quantify a target molecule in a tissue in an analysis of said tissue.

A subject of the invention is therefore a use of a dilution range of a standard molecule in a reconstituted tissue to quantify a target molecule in a tissue of interest identical to the reconstituted tissue of the dilution range.

Similarly, the subject of the invention is a method for detecting and quantifying at least one target molecule in at least one tissue of interest comprising the following steps:

a) analysing a slice of the tissue of interest, so as to obtain a signal representative of the quantity of target molecule in said slice; and b) determining the quantity of target molecule in said tissue by using a dilution range of a standard molecule in a reconstituted tissue identical to the tissue of interest.

The dilution range used can be obtained according to the steps (i) to (v) described above by using a tissue identical to the tissue of interest to produce the tissue homogenate.

The tissue is understood to be at least a part of at least one biological tissue (plant or animal).

In one embodiment, it is possible to quantify at least one target molecule in a tissue sample comprising a number of tissues, and notably a number of adjacent tissues in an organism. For example, the slice of the tissue sample may consist of a slice of a whole animal or a portion of an animal, including at least one organ or at least one organ portion. Notably, the analysis of a slice of a whole animal can make it possible to compare, in the same sample, the distribution of one or more target molecules in different tissues of said animal. In this case, to determine the quantity of a given target molecule in each of the tissues of the tissue sample, a dilution range of said target molecule specific to the tissue considered is used.

The step a) of analysis of the target molecule can be done by any analysis method, such as mass spectrometry, and notably by using direct mass spectrometry (MS) or tandem mass spectrometry ($MS^n$, MRM, SRM), analysis by fluorescence, autoradiography, etc.

The method according to the invention can advantageously be used with mass spectrometry. In this case, it is possible to use different ionization sources, MALDI (Matrix-Assisted Laser Desorption-Ionization), LDI (Laser Desorption-Ionization), LESA (Liquid Extraction Surface Analysis), LAESI (Laser Ablation Electrospray Ionization), DESI (Electrospray Desorption-Ionization), NanoDESI, etc., combined with different types of analysers, TOF (Time Of Flight), Orbitrap, FTICR (Fourier Transform Ion Cyclotronic Resonance), etc. This imaging technique makes it possible to quantify the target molecule directly on the ion density map obtained for the tissue sample, corresponding to the spatial distribution of the target molecule in said tissue sample. It is in fact possible to transfer the signal obtained on said ion density map to the corresponding dilution range.

Some mass spectrometry techniques, such as MALDI or ME-SIMS, require a slice of the tissue sample to be analysed to be first covered with a matrix comprising small organic molecules that are absorbent in the UV. This matrix allows for the desorption and ionization of the molecules present on the sample.

The method according to the invention can be used regardless of the matrix chosen. These matrices take a solid form (crystallization on the sample) or liquid form, and are said to be ionic or non-ionic. The choice of the matrix is made according to the mass series analysed. They are more often than not prepared extemporaneously in a solvent-aqueous solution mixture.

Several matrix deposition methods are possible, notably manual deposition using a pipette, which makes it possible to deposit an accurate volume of matrix directly on the tissue. It is also possible to deposit the matrix by spray or vaporization, the matrix being sprayed or vaporized directly onto the tissue sample using a robot, or by hand. Similarly, deposition by microdroplets, by which the matrix is applied in spots to the tissue sample via piezoelectric, acoustic or syringe pump systems, can be envisaged. It is also possible to deposit the matrix by screening, in order to deposit the matrix in solid form.

The experimental parameters, such as the mass range and/or the laser intensity, are advantageously set in such a way as to optimize the detection of the target molecule in terms of intensity, sensitivity and resolution.

The next step is to acquire the signal representative of the quantity of target molecule in said slice.

In the case where the analysis consists of acquiring the mass spectrum, different spectral characteristics can be used, such as signal in the step b), and notably the intensity of the peaks of the mass spectrum, the signal-noise ratio (S/N), the area of the peak, etc. Obviously, the spectral characteristic used to quantify the target molecule is the same as the spectral characteristic used for the preparation of the standard range. And, more generally, the characteristic of the signal taken into account to quantify the target molecule is the same as the characteristic of the signal used for the preparation of the standard range.

In certain conditions, it is, moreover, possible to normalize the spectral characteristic or characteristics based on a normalization factor that is determined by the technology.

For example, in the case where the method according to the invention uses mass spectrometry imaging of the MALDI type, a step of evaluating the uniformity of the matrix deposition on the sample is provided. In practice, the signal corresponding to the matrix used can give information as to the quality/uniformity of the deposition of said matrix. The matrix defects on the surface of the sample can then be correlated with the non-detection or with the loss of intensity of the signal from the target molecule in the sample considered.

The evaluation of the uniformity of the matrix can be done according to qualitative criteria by observing, by optical microscope, the uniformity of the deposition on the surface of the sample, and/or according to quantitative criteria, by tracking the variations of the signal relative to the matrix itself on the sample.

As for the qualitative criteria, it is essential to ensure that the matrix has been deposited as uniformly as possible on the surface considered, that there are no areas devoid of matrix and that its crystallization is optimal.

For the quantitative evaluation of the uniformity of the matrix deposition, the matrix is considered as a specific molecule whose signal is detected in the same way as the signal from the target molecule, at the time of analysis of a sample. The signal from the matrix molecule is then compared to its reference signal. The reference signal of the matrix corresponds in this case to the signal emitted by the matrix on a reference matrix deposition, that is to say on a sample and on an analysis support that are used specifically to measure the reference signal of the matrix.

By these additional steps, the signal from the target molecule is validated and normalized to take account of the variation of the quality of the matrix deposition that can affect the spectral characteristics of the latter.

This inclusion of the matrix effect can be particularly advantageous in the case where there is a desire to track the trend of the presence of a target molecule over time, the quality of the matrix deposition being able to vary from one sample to another.

The standard range used can be produced using a standard molecule identical to the target molecule. It is also possible to use a standard molecule that is different from the target molecule, and that has similar physical-chemical properties. It is also possible to use the target molecule labeled with an isotope as standard molecule for the preparation of the dilution range.

Depending on the analysis methods used, the target molecule may be labeled. For example, in the case of a fluorescence analysis, the target molecule is labeled by a fluorescent molecule. Similarly, in the case of an analysis by autoradiography, the target molecule is radiolabeled.

The method according to the invention can be used for the analysis of all kinds of molecules, such as peptides, polypeptides, proteins, amino acids, nucleic acids, lipids, metabolites, etc., and, generally, for any pharmaceutically or otherwise active molecule and, notably, in the case of an analysis by mass spectrometry, for any molecule which can be ionized.

In the case where the target molecule is a protein of high molecular weight, it is possible to perform an enzymatic pretreatment of the target module, in order to split it up into a number of peptides. The detection and the quantification are then performed for at least one of the peptides obtained from said enzymatic digestion, representative of said protein. For example, trypsin can be used, in order to split the target protein into a number of previously identified peptides.

Similarly, it is possible to treat the tissue to be analysed with at least one solvent and/or at least one detergent before the detection step, so as to eliminate molecules responsible for background noise. For example, a wash in chloroform makes it possible to remove certain classes of lipids. A wash in ethanol, for its part, allows for a better detection of molecules of low masses. These two washes advantageously make it possible to remove certain molecules, notably lipidic molecules, thus favouring the detection of new ions directly on the tissue sample.

The method according to the invention can also be used to quantify at least two different target molecules on the same tissue and/or on the same tissue sample comprising a number of tissues, simultaneously or not. Different dilution ranges are then used, each specific to the target molecule considered and to the tissue considered.

Similarly, the same target molecules can be detected and quantified simultaneously on different tissues, by analysing by mass spectrometry, or otherwise, a tissue sample comprising a number of tissues. In this case, for each of the tissues of the sample, for example of the organs in a whole animal slice, the dilution range produced for said target molecule in the corresponding tissue/organ is used.

The invention also proposes a method for validating a method for detecting and/or quantifying at least one target molecule in a tissue from a slice of said tissue, comprising the steps consisting of:

(x) grinding a tissue identical to the tissue to which the detection and/or quantification method must be applied, to obtain a tissue homogenate;

(xi) mixing a standard molecule with at least two samples of the tissue homogenate from the step (x), said standard molecule being in the same known concentration for the at least two samples of tissue homogenate;

(xii) conditioning the samples of tissue homogenate obtained from the step (xi) so as to be able to slice said conditioned samples of tissue homogenate;

(xiii) analysing at least one slice of each of the conditioned samples of tissue homogenate from the step (xii), so as to obtain a signal representative of the standard molecule for each of the slices; and (xiv) comparing the signals obtained for each of the slices with one another.

Such a method makes it possible to check, notably upstream of a detection and/or quantification method, that a given reconstituted tissue, that is to say a conditioned tissue homogenate, is representative of the corresponding whole tissue. This method makes it possible to evaluate the sensitivity of the detection and/or quantification method according to the invention for a given molecule and a given sample, notably by means of the LOD.

Advantageously, the step (xi) is conducted on at least three samples of tissue homogenate.

The comparison of the signals performed in the step (xiv) advantageously makes it possible to evaluate the reproducibility of the detection and/or of the quantification of a given molecule in a given tissue, by computing the relative standard deviation RSD, given as a decimal value or a percentage.

Obviously, all the particular ways of producing the tissue homogenate, of conditioning, of preparing the standard molecule, of analysis, etc., like the nature of the tissue and/or of the standard molecule, as explained above for the preparation of the dilution range, can be applied for the implementation of the validation method.

The invention also proposes a method for controlling the quality and/or the reproducibility of a method for detecting and/or quantifying at least one target molecule in a tissue of interest from a slice of said tissue, comprising the steps consisting of:

(xx) grinding a tissue identical to the tissue of interest, to obtain a tissue homogenate;

(xxi) mixing a known concentration of a standard molecule with a sample of the tissue homogenate from the step (xx);

(xxii) conditioning the sample of tissue homogenate obtained from the step (xxi) so as to be able to slice said conditioned sample of tissue homogenate;

(xxiii) for each slice of the tissue of interest to be analysed, simultaneously analysing a slice of the conditioned sample of tissue homogenate from the step (xxii), so as to obtain, each time, a signal representative of the standard molecule for the slice of the conditioned sample of tissue homogenate from the step (xxii) and a signal representative of the target molecule for the tissue of interest; and (xxiv) comparing the signals obtained for each of the slices of the conditioned sample of tissue homogenate from the step (xxii).

Thus, according to the invention, a slice of doped tissue, and notably of organ, blood, plasma, serum, urine, plant tissue, etc., containing one or more compounds, can be used as quality control for each analysis performed in the context of a detection and/or quantification study, and/or to monitor the performance of an analytical instrument.

The tissue of interest should be understood to be the tissue in which the detection and/or quantification is to be done.

The step (xxiii) is advantageously performed by depositing, on the same support, and notably on the same slide, the slice of the tissue of interest to be analysed and the slice of the doped/conditioned sample of tissue homogenate. The same support preparation conditions (for example the matrix used, the quality of its deposition) and analysis conditions are thus applied to both slices.

The variation of the signal obtained in the step (xxiv) can be normalized, for example by using the corresponding weighting average, to take account of the variations of the parameters such as the matrix effect.

Such a method can, for example, be used for the relative quantification of a molecule by simple comparison of the signal from one slice with another, for monitoring the trend of the bioavailability of a molecule in time, etc.

Therefore it is also an object of the invention to propose a method for relatively quantifying at least one target molecule in a tissue of interest, said method comprising the steps consisting of:

(xxx) grinding a tissue identical to the tissue of interest, to obtain a tissue homogenate;

(xxxi) mixing a known concentration of a standard molecule with a sample of the tissue homogenate from the step (xxx);

(xxxii) conditioning the sample of tissue homogenate obtained from the step (xxxi) so as to be able to slice said conditioned sample of tissue homogenate;

(xxxiii) for each slice of the tissue of interest to be analysed, simultaneously analysing a slice of the conditioned sample of tissue homogenate from the step (xxxii), so as to obtain, each time, a signal representative of the standard molecule for the slice of the conditioned sample of tissue homogenate from the step (xxxii) and a signal representative of the target molecule for the tissue of interest;

(xxxiv) computing, for each slice of the tissue of interest to be analysed, the ratio of signal from the target molecule in the tissue of interest to signal from the standard molecule in the reconstituted tissue; and (xxxv) comparing the ratios obtained for each slice of the tissue of interest to obtain a relative quantification of the target molecule.

Obviously, all the particular ways of producing the tissue homogenate, of conditioning, of preparing the standard molecule, of analysing, etc., like the nature of the tissue and/or of the standard molecule, as explained above for the preparation of the dilution range, can be applied for the implementation of the method for controlling the quality and/or the reproducibility according to the invention, the relative or absolute quantification method and the method for evaluating the smallest quantity of a target molecule that can be detected and/or that can be quantified in a tissue according to the invention.

According to the invention, the normalization of the source data, that is to say the correlations between a signal from a target molecule in a tissue and the corresponding concentration from a dilution range of a standard molecule in an identical reconstituted tissue, for the purpose of quantification, can be performed by means of a computer program incorporating all or part of these factors.

This computer program, or data reprocessing software, can advantageously weight these values by the matrix effect or by the standard (isotopic or not) when processing the image in the case of imaging by mass spectrometry.

Advantageously, a computer program according to the invention can compare the intensity of the target molecule on the tissue of interest with the intensity of the standard molecule on the reconstituted tissue, so as to arrive at a ratio making it possible to perform a relative quantification of the compound of interest between different tissues by comparison of the ratios obtained for each of them.

Another subject of the invention is therefore a computer-readable data medium comprising instructions that can be executed by the computer, such as the reading of raw data obtained from the analysis by mass spectrometry, and/or the determination of the calibration curve, and/or the normalization of the raw data by the latter in order to obtain a quantitative value of the target molecule. Advantageously, these instructions that can be executed by the computer are adapted to enable a computer system to execute at least the step b) of the quantification method according to the invention and/or the step (xxiv) of the method for controlling the quality/reproducibility of a detection/quantification method, and, where appropriate, the weighting step using the results according to the step (xxiv), like the step (xxxiv) and/or the step (xxxv) of the relative quantification method according to the invention.

The data medium advantageously comprises at least one standard range of at least one target molecule in at least two different tissues. Preferentially, in the case of biological samples, such as a slice of a whole animal, the database comprises the dilution range of at least one target molecule in the different tissues of said sample.

The data medium may also comprise a database of the reference signal of at least one matrix used in mass spectrometry imaging. Thus, it is possible to take account of the matrix effect when analysing the sample by imaging implementing the data medium.

EXAMPLES

Equipment and Method

Equipment

Propranolol from Sigma-Aldrich was used to produce a $1.10^{-10}$ mol/$\mu$l propranolol solution.

Six different precise sub-volumes of this solution are taken, which will each be added to a sample of tissue homogenate so as to obtain a concentration in the samples of 0, 2.8, 5.6, 11.2, 22.4 and 44.8 $\mu$g/g (Table 1).

Samples of Tissue Homogenate

Male mice of Swiss type weighing 25-40 g from Charles River (France) were used.

For the preparation of the dilution range, two kidneys from a control mouse (that is to say not having undergone any particular treatment) are taken. The two kidneys are ground mechanically using a scalpel, in a vessel previously sterilized and placed on ice. Once the kidney homogenate is obtained, said homogenate is distributed approximately in six 1.5 ml tubes, and each of the six samples of tissue homogenate is weighed (Table 1).

To each of the samples of tissue homogenate, one of the particular sub-volumes of the propranolol solution is added.

Table 1 below gives all the specific data for the six samples of kidney homogenate.

TABLE 1

Preparation of the samples of kidney homogenate used to produce a dilution range representative of the propranolol in the kidney.

| Number of sample of kidney homogenate | Homogenate weight (g) | Volume of propranolol (µl) of a $1.10^{-10}$ mol/µl propranolol solution added per sample | Final propranolol concentration in the sample (µg/g) |
|---|---|---|---|
| 1 | 0.7 | 61.7  | 2.8  |
| 2 | 0.4 | 66.4  | 5.6  |
| 3 | 0.7 | 246.8 | 11.2 |
| 4 | 0.4 | 265.8 | 22.4 |
| 5 | 0.4 | 637.8 | 44.8 |
| 6 | 0.5 | 0.0   | 0.0  |

Preparation of the Reconstituted Tissues

Each tube containing a sample of kidney homogenate is vortexed for 1 hour at ambient temperature, so as to uniformly distribute the propranolol in said samples.

Figure 1A:
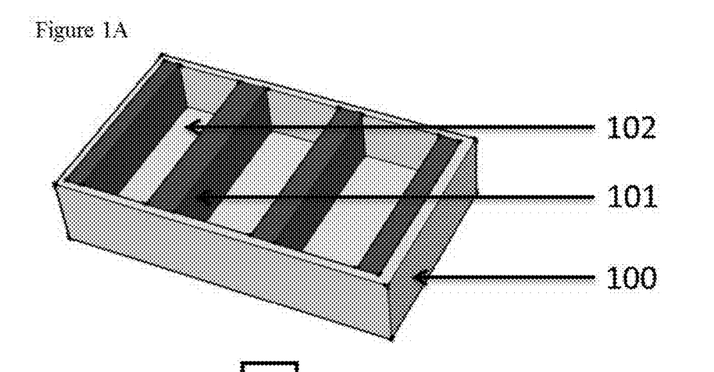
FIGS. 1A and 1B. A schematic representation of an embodiment of the mould (FIG. 1A) with a number of compartments that can be used when implementing the method for preparing a dilution range according to the invention, each compartment being able to receive a sample of tissue homogenate doped with a specific concentration of standard molecule; and a schematic representation of the samples of tissue homogenate conditioned and stripped from the mould after freezing in the mould (FIG. 1B), each sample of tissue homogenate being separated from an adjacent sample by a partition.

A mould 100 of aluminium is used, like the one represented in FIG. 1A, provided with 7 transverse partitions 101 so as to form six compartments 102 extending successively in a greater dimension of said mould (only three compartments are formed in the mould of FIG. 1A). The mould is placed in liquid nitrogen so as to rapidly freeze the kidney homogenate. The mould is then placed for 1 hour at −80° C.

Figure 1B:
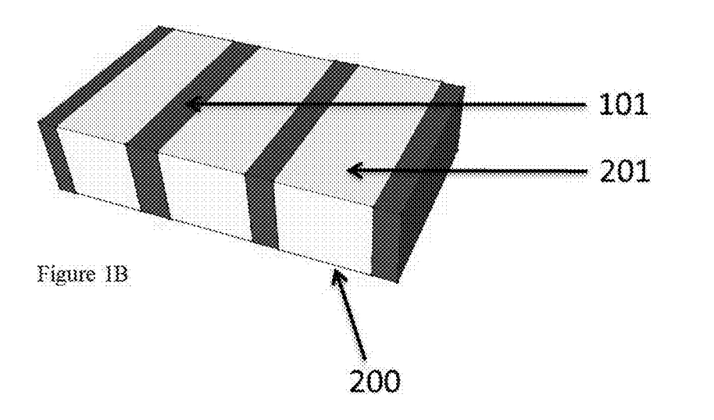

The block 200 of reconstituted, or conditioned, tissues (that is to say the frozen samples of kidney homogenate) is then stripped from the mould (FIG. 1B). The reconstituted tissues 201 are sliced using a cryostat cooled to −22° C. to a thickness of 20 µm. Depending on the requirements, on the same slice, all the tissues 201 of the series are kept separated from one another by the partitions 101, or the portion corresponding to the desired reconstituted tissue(s) is separated from the rest of the slice.

Example 1: Validation of the "Reconstituted Tissue" Model

In this example, the aim is to demonstrate that reconstituted tissues, formed by tissue homogenates which have been frozen, form a model representative of the corresponding whole tissue.

For this, the density and the molecular extinction coefficient (TEC) of a reconstituted kidney according to the invention and of a whole kidney are measured and compared.

Ten slices of the reconstituted tissue No. 6 (control, Table 1) are separated and each placed on a support (slide ITO2).

Ten 20 µm slices of tissue are also produced from a whole kidney taken from another control mouse, kept at ambient temperature. Each slice is arranged on a support (slide ITO3).

The supports are scanned simultaneously in an HP Scanjet G4010 scanner at 2400 dpi and the image is stored in jpeg format.

The average density of the reconstituted kidney slices and of the whole kidney slices is then computed, as explained in Table 2 below. More specifically, the average value of the surface, of the height, of the volume and of the weight of the reconstituted kidney is computed from values obtained for each of the ten slices of the control reconstituted tissue. Similarly, the average value of the surface, of the height, of the volume and of the weight of the whole kidney is computed from the values obtained for each of the ten corresponding slices.

It is found that the densities of the two tissues are substantially identical, since they differ only by 0.04 mg/mm³ (Table 2).

In order to calculate the TEC for the reconstituted tissue and for the whole tissue, MALDI DHB matrix (40 mg/ml methanol/TFA 0.1% 1/1) containing 10 pmol of propranolol is sprayed using a robotized system (SunCollect) onto the two batches of ten slides ITO2 and ITO3 used to compute the density.

Each tissue slice is then analysed by MALDI imaging using an Autoflex speed LRF (Bruker, Daltonics).

The intensities of the propranolol (m/z 260.2) of each batch of slices are averaged on the slice of tissue and on the support.

The TEC can then be calculated by using the values of the intensity of the signal emitted by the propranolol on the slide and on the tissues respectively, according to the mathematical formula:

$$TEC = \frac{Int(\text{slide})_x}{Int(\text{tissue})_x}$$

As shown in Table 2, it is found that the average values of TEC obtained for the reconstituted kidney and for the whole kidney are identical.

The reconstituted kidney therefore has the same density and the same tissue extinction coefficient as a whole kidney.

TABLE 2

Comparison of the densities and of the TECs in a reconstituted kidney and a whole kidney.

|  | Reconstituted kidney slice | Whole kidney slice |
|---|---|---|
| Pixels | 121637 | 229374.2 |
| Surface (mm²) | 12.1637 | 22.93742 |
| Height (mm) | 0.02 | 0.02 |
| Volume (mm³) | 0.243274 | 0.4587484 |
| Weight (mg)/slice | 0.17 | 0.305 |
| Density (mg/mm3) | 0.7 | 0.66 |
| TEC | 1.9361 | 1.922125 |
| Standard deviation | 0.162580886 | 0.408923827 |
| TEC error % | 8.4 | 21.3 |

The propranolol therefore behaves identically in a reconstituted kidney and in a whole kidney. The use of a reconstituted tissue for the preparation of a dilution range of a molecule according to the invention can thus subsequently make it possible to reliably quantify said molecule in a corresponding whole tissue.

Example 2: Preparation of a Dilution Range of Propranolol for the Kidney

A slice comprising the succession of samples of kidney homogenate, and therefore having the six successive concentrations of propanolol (in the order shown in Table 1), is placed on a support (slide ITO1).

MALDI DHB matrix (40 mg/ml methanol/TFA 0.1% 1/1) is sprayed onto the slice of tissue using a robotized system (SunCollect).

Each portion of the slice representing a sample of kidney homogenate is then analysed by mass spectrometry imaging using an Autoflex speed LRF (Bruker, Daltonics).

A number of regions of interest (ROI), of equal dimensions, are then delimited on the image obtained by mass spectrometry for each of the samples of tissue homogenate.

The intensity of the peaks of the mass spectrum is chosen for use as a reference signal. The intensities of the peaks of the mass spectrum of the propranolol are recovered for each ROI, for each of the samples of tissue homogenate. Also, for each sample of tissue homogenate, an average intensity (average ROI) is computed from the intensity obtained for all the corresponding ROIs.

The average intensities of the peaks of the mass spectrum of the propranolol for each point of the dilution range, that is to say for each sample of tissue homogenate, are listed in Table 3.

TABLE 3

Average intensities obtained by MALDI imaging for each point of the dilution range of propranolol (m/z 260.2) in a reconstituted kidney

| Number of sample of kidney homogenate | Final propranolol concentration in the reconstituted tissue (µg/g) | Intensity |
|---|---|---|
| 1 | 2.8 | 9273.9 |
| 2 | 5.6 | 18223.0 |
| 3 | 11.2 | 37269.0 |
| 4 | 22.4 | 74191.0 |
| 5 | 44.8 | 145396.6 |
| 6 | 0.0 | 500.3 |

A calibration curve can then be drawn. This calibration curve can be used subsequently, in a method for quantifying the propranolol in a kidney. It is sufficient to correlate the intensity of the peak of the mass spectrum obtained for the propranolol in the kidney analysed with a concentration on said calibration curve.

Figure 2:
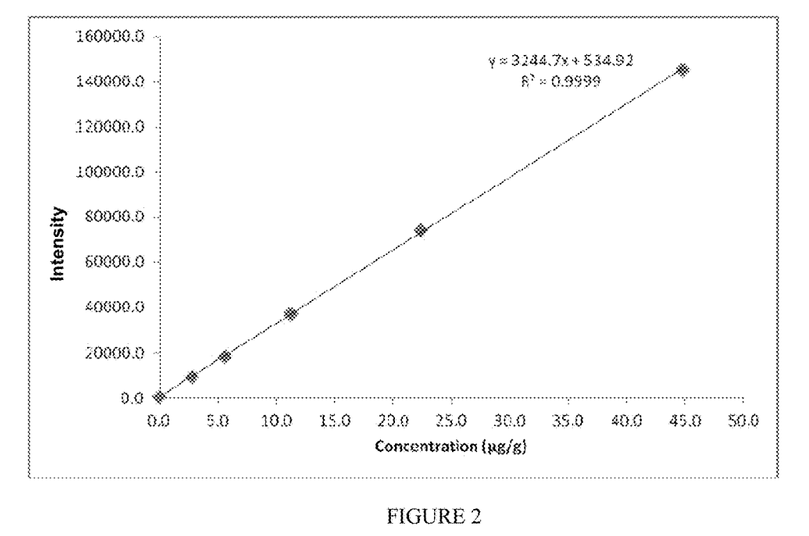
FIG. 2: A calibration curve of a standard molecule (propranolol) in a tissue (kidney) obtained according to the preparation method of the invention, representing the concentration ($\mu g/g$—x axis) of propranolol as a function of the intensity emitted by the propranolol (y axis) in mass spectrometry.

For example, a calibration curve is plotted, representing the concentration of propranolol in the tissue (µg/g) as a function of the intensity of the peak of the mass spectrum (FIG. 2). The equation for the trend curve of all the points of the dilution range, or cloud of points, is computed in the format y=ax+b using a graphic reprocessing software, such as Excel.

In the example described, the equation for the trend curve is y=3244.7x+534.92. This equation subsequently allows for the quantification of the molecule.

Similarly, the determination coefficient (here $R^2$=0.9999), which is an indicator which makes it possible to judge the quality of a linear, single or multiple regression, is computed. The closer this coefficient is to 1, the more linear the trend curve becomes.

Example 3: Quantification of the Propranolol in a Treated Mouse Kidney

A mouse kidney treated with 7.5 mg/kg of propranolol, and sacrificed 20 minutes post-administration, is taken.

Three 20 µm thick tissue slices are produced from the kidney and are each deposited on a support (slide ITO).

MALDI DHB matrix (40 mg/ml methanol/TFA 0.1% 1/1) is sprayed using a robotized system (SunCollect) onto the slices.

Each slice is analysed by mass spectrometry imaging, using an Autoflex speed LRF (Bruker, Daltonics). The average intensity of the peaks of the mass spectrum of the propranolol (m/z 260.2) is computed, by once again using a number of ROIs on each slice, all dimensions being the same.

The average intensity value obtained is 19633.3.

The propranolol concentration in the kidney is quantified using the calibration curve equation (FIG. 2), by including the average intensity value obtained on said straight line. The propranolol here is in a concentration of 5.9 µg/g of tissue.

Example 4: Evaluation of the Limit of Detection of the Propranolol in the Kidney In the context of this usage, a dilution range or a dilution point of one or more molecules of interest in reconstituted tissues is used in order to evaluate the detection of the molecule or molecules using a chosen analytical method.

In this example, a dilution range is produced from nine different precise sub-volumes of the propranolol solution, which are each added to a sample of kidney homogenate, in such a way as to obtain a concentration in the samples of 0, 0.3, 0.7, 1.4, 2.8, 5.6, 11.2, 22.4 and 44.8 µg/g.

A slice comprising the succession of samples of kidney homogenate, and therefore having nine successive concentrations of propanolol (in the order presented in Table 4), is placed on a support (slide ITO).

In the context of an analysis of the slides by MALDI-TOF imaging, it is possible, by virtue of the invention, to fine-tune the protocol for preparing the tissues which will be analysed in a preliminary phase. In practice, it is possible to use the prepared series and to perform a number of preparation tests to evaluate, for example, the influence of the thickness of the slices or even the choice of the matrix and/or its method of deposition on the signal obtained.

In this example, the optimum thickness is set at 20 µm and the most effective MALDI matrix is DHB at 40 mg/ml methanol/TFA 0.1% 1/1.

Each portion of the slice representing a sample of kidney homogenate is then analysed by mass spectrometry imaging or by direct analysis using an Autoflex speed LRF (Bruker, Daltonics).

In the context of an acquisition in imaging mode, a number of regions of interest (ROI), of equal dimensions, are delimited on the image obtained by mass spectrometry for each of the samples of tissue homogenate.

In the context of an acquisition in direct analysis mode, an average spectrum representative of each point of the series is obtained.

The intensity of the peaks of the mass spectrum is chosen for use as a reference signal. The intensities of the peaks of the mass spectrum of the propranolol are recovered for each of the samples of tissue homogenate. Also, for each sample of tissue homogenate, an average intensity is therefore obtained.

The average intensities of the peaks of the mass spectrum of the propranolol for each point of the dilution range, that is to say for each sample of tissue homogenate, are listed in Table 4.

TABLE 4

Average intensities obtained by MALDI imaging for each point of the dilution range of propanolol (m/z 260.2) in a reconstituted kidney

| Number of sample of kidney homogenate | Final concentration of propranolol in the reconstituted tissue (µg/g) | Intensity |
|---|---|---|
| 1 | 0.0 | 500.3 |
| 2 | 0.3 | 520.6 |
| 3 | 0.7 | 2806.2 |
| 4 | 1.4 | 5077.5 |
| 5 | 2.8 | 9273.9 |
| 6 | 5.6 | 18223.0 |
| 7 | 11.2 | 37269.0 |
| 8 | 22.4 | 74191.0 |
| 9 | 44.8 | 145396.6 |

Thus, it is possible to evaluate the limit of detection of the compound in the chosen medium, which is here 0.7 µg/g. This limit of detection is set in this example as being the lowest concentration for which the compound is detected with a signal/noise ratio greater than 3. Note that it is also possible to determine the limit of quantification.

Also, if a quantification of the compound in a treated tissue had to be performed, it can be evaluated in this example that the analytical method is linear to 3 log.

More generally, the invention makes it possible to evaluate a number of parameters before the preparation of the test systems in vivo, such as:

The thickness of the tissue slices
The MALDI matrix best suited to the desorption and the ionization of the compounds
The matrix deposition method
The limit of detection and of quantification of the compound or compounds in a reference medium
The range of linearity of the analytical method in order to perform the quantification of the compound or compounds, etc.

Example 5: Control of the Quality and of the Reproducibility of Analyses in MALDI Mass Spectrometry Imaging In this example, the aim is to evaluate the quality and the reproducibility of an analysis in MALDI imaging.

A slice of kidney homogenate comprising a known concentration of propanolol (5.6 µg/g) is deposited on the same support (slide ITO) as the sample of interest. Note that this reconstituted kidney homogenate is used in the context of all the analyses for which the reproducibility is to be evaluated.

During each analysis of the samples of interest, for which the same preparation method and the same analytical method are used, a slice of the quality control is analysed at the same time in MALDI imaging.

Figure 3:
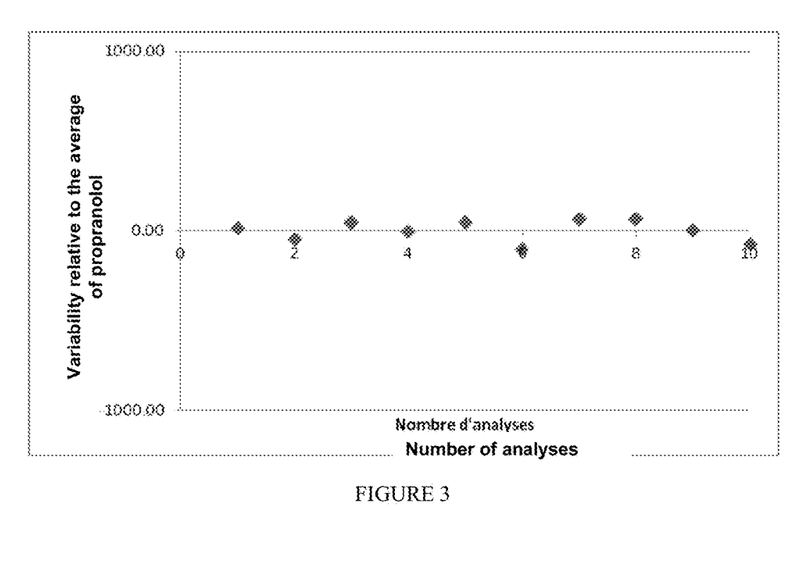
FIG. 3: A weighting straight line showing the analytical variability in MSI measured using quality controls of kidney tissue type reconstituted and doped with the same concentration of propranolol.

The value of the average intensity of the propanolol is therefore obtained for each analysis and it is thus possible to monitor the reproducibility of the analyses. Thus, in the context of 10 analyses of tissues of interest, a slice of reconstituted kidney doped with propanolol at 5.6 µg/g has been added. FIG. 3 shows the variability obtained in the context of 10 constituent analyses in one and the same study.

It is thus possible to monitor the experimental variabilities or even to normalize the values obtained for each analysis relative to this quality control in order to relatively quantify compound(s) of interest between different analyses.

It is also possible to judge the quality of the preparation of the tissues (more particularly of the deposition of the MALDI matrix) and the quality of the analytical performance levels of the instrument used. Note that maintenance can be determined as a function of the results of these quality controls.

The invention claimed is:

1. A method for detecting the distribution and quantifying by mass spectrometry imaging at least one target molecule in at least one tissue from a plant or animal comprising:
   (a) obtaining a tissue sample from said plant or animal, slicing said tissue into tissue slices and performing mass spectrometry imaging analysis on a tissue slice and detecting a mass spectrum signal representative of said at least one target molecule in said tissue slice;
   (b) using the mass spectrum signal of the at least one target molecule to determine the quantity and distribution of said at least one target molecule in the tissue sample by correlating the mass spectrum signal of said at least one target molecule detected in said tissue slice with a mass spectrum signal in a calibration curve that is representative of a concentration of said at least one target molecule in a slice of a solidified sample of a tissue homogenate, wherein said calibration curve is obtained according to the following steps:
   (i) preparing a tissue homogenate of a tissue identical to the tissue of step (a);
   (ii) adding a first known concentration of said at least one target molecule to a first sample of said tissue homogenate prepared in step (i);
   (iii) adding a second known concentration of said at least one target molecule to a second sample of said tissue homogenate prepared in step (i), said second known concentration of said at least one target molecule differing from the first known concentration of said at least one target molecule;
   (iv) optionally repeating steps (ii) and (iii) with at least one additional sample of tissue homogenate from the step (i) and at least one additional known concentration of said at least one target molecule that differs from said first and said second concentrations of said target molecule;
   (v) solidifying the samples of tissue homogenates containing known concentrations of said at least one target molecule;
   (vi) slicing with substantially identical thickness said solidified samples of tissue homogenates containing different known concentrations of said at least one target molecule; and
   (vii) performing mass spectrometry analysis on said sliced solidified samples of tissue homogenates for said at least one target molecule, and detecting the signal representative of each concentration of said at least one target molecule in each slice of the solidified sample of tissue homogenate.

2. The method according to claim 1, in which the step of solidifying samples of said tissue homogenates comprises freezing and/or coating said sample of tissue homogenate.

3. The method according to claim 1, wherein the tissue homogenates containing said known concentrations of said at least one target molecule are mixed to uniformly distribute said at least one target molecule in said tissue homogenates.

4. The method according to claim 1, in which at least two different target molecules are simultaneously detected in said tissue slice and said tissue homogenate slices.

5. The method according to claim 1, in which the target molecule is a protein, a peptide, a polypeptide, an amino acid, a nucleic acid, a lipid, a drug, a pharmaceutically or biologically active molecule or a metabolite.

6. The method according to claim 1, wherein the signal associated with the mass spectrum of the target molecule is the intensity of the peak, the area of the peak or the signal/noise ratio of the mass spectrum of the target molecule.

7. The method according to claim 1, in which the target molecule is isotopically labeled.

8. The method according to claim 1, wherein the target molecule is detected directly on a slice of a whole animal.

9. The method according to claim 1, wherein the signal is selected from the group consisting of intensity of the peak, area of the peak or signal/noise ratio of said mass spectrum.

10. The method according to claim 1, wherein said method further comprises the step of reconstructing an image of the distribution of the at least one target molecule in the tissue slice of step (a) by correlating the mass spectrum signal representative of said at least one target molecule detected in said tissue slice with a mass spectrum signal representative of a concentration of said at least one target molecule in a tissue homogenate slice of steps (i)-(v).

11. A method for validating a method for detecting at least one target molecule in a tissue from a slice of said tissue, comprising the steps of:
(a) preparing a tissue homogenate containing said at least one target molecule comprising:
(i) preparing a tissue homogenate of a tissue;
(ii) adding a known concentration of said at least one target molecule to at least two samples of said tissue homogenate prepared in step (i);
(iii) mixing the target molecule containing tissue homogenates of step (ii);
(iv) solidifying the samples of tissue homogenates containing known concentrations of said at least one target molecule; and
(v) slicing with substantially identical thickness said solidified samples of tissue homogenates of step (iv); and
(b) performing mass spectrometry analysis on sliced solidified samples of tissue homogenates and detecting the signal for each concentration of said at least one target molecule in each tissue homogenate slice.

12. A method for detecting the smallest quantity of a target molecule that can be detected in a tissue, said smallest quantity having a signal/noise value greater than or equal to 3, comprising:
(a) preparing a dilution range of said at least one target molecule, said preparing of said dilution range comprising:
(i) preparing a tissue homogenate of said tissue;
(ii) adding a first known concentration of said at least one target molecule to a sample of said tissue homogenate prepared in step (i) and mixing said tissue homogenate and said at least one target molecule;
(iii) adding a second known concentration of said at least one target molecule to a second sample of said tissue homogenate prepared in step (i), said second known concentration of said at least one target molecule differing from the first known concentration of said at least one target molecule and mixing said tissue homogenate and said second concentration of said at least one target molecule;
(iv) optionally repeating steps (ii) and (iii) with at least one additional sample of tissue homogenate from step (i) and at least one additional known concentration of said at least one target molecule that differs from said first and said second concentrations of said target molecule;
(v) solidifying the samples of tissue homogenates containing known concentrations of said at least one target molecule;
(vi) slicing with substantially identical thickness said solidified samples of tissue homogenates containing different concentrations of said at least one target molecule; and
(b) performing mass spectrometry analysis on said sliced solidified samples of tissue homogenates and detecting a signal for each concentration of said at least one target molecule in each tissue homogenate slice.

13. A method for detecting the limit of quantification (LOQ) of a target molecule in a tissue, whereby the smallest signal exhibiting a signal/noise value greater than or equal to 3 times the signal/noise value of the smallest detectable signal and having a value of least 10 is the LOQ, from a specific dilution range of the target molecule comprising:
(a) preparing a dilution range of said at least one target molecule, said preparing of said dilution range comprising:
(i) preparing a tissue homogenate of a tissue;
(ii) adding a first known concentration of said at least one target molecule to a sample of said tissue homogenate prepared in step (i) and mixing said tissue homogenate and said at least one target molecule;
(iii) adding a second known concentration of said at least one target molecule to a second sample of said tissue homogenate prepared in step (i), said second known concentration of said at least one target molecule differing from the first known concentration of said at least one target molecule and mixing said tissue homogenate and said second concentration of said at least one target molecule;
(iv) optionally repeating steps (ii) and (iii) with at least one additional sample of tissue homogenate from step (i) and at least one additional known concentration of said at least one target molecule that differs from said first and said second concentrations of said target molecule;
(v) solidifying the samples of tissue homogenates containing known concentrations of said at least one target molecule;
(vi) slicing with substantially identical thickness said solidified samples of tissue homogenates containing different known concentrations of said at least one target molecule; and
(vii) performing mass spectrometry analysis on said sliced solidified samples of tissue homogenates and detecting said at least one target molecule in each tissue homogenate slice and in said tissue slice.

14. A method for controlling the quality and/or the reproducibility of a method for detecting at least one target molecule in a tissue of interest from a slice of said tissue, comprising the steps of:
(a) preparing a tissue homogenate sample of a tissue;
(b) adding a known concentration of said at least one target molecule to said tissue homogenate prepared in step (a);
(c) solidifying the sample of tissue homogenate containing the known concentration of said at least one target molecule;
(d) slicing with substantially identical thickness said solidified sample of tissue homogenate containing said known concentration of said at least one target molecule; and
(e) simultaneously performing mass spectrometry analysis on said sliced solidified sample of tissue homogenate and a tissue slice containing said at least one target molecule and detecting a signal representative of the target molecule in the sliced solidified tissue homogenate and a signal representative of the target molecule for the tissue slice containing said at least one target molecule.

15. A method for detecting at least one target molecule in a tissue of interest, comprising the steps of:
   (a) preparing a tissue homogenate of a tissue of interest;
   (b) adding a known concentration of said at least one target molecule to a sample of said tissue homogenate prepared in step (a);
   (c) solidifying the samples of tissue homogenates containing said known concentration of said at least one target molecule;
   (d) slicing with substantially identical thickness said solidified samples of tissue homogenates containing said known concentration of said at least one target molecule; and
   (e) simultaneously performing mass spectrometry analysis on said sliced solidified sample of tissue homogenate and a tissue slice containing said at least one target molecule and detecting a signal representative of the target molecule in the sliced solidified tissue homogenate and a signal representative of the target molecule for the tissue slice containing said at least one target molecule.

16. A method for detecting and quantifying at least one target molecule in at least one tissue comprising:
   (a) performing mass spectrometry analysis on a tissue slice and detecting a mass spectrum signal representative of said at least one target molecule in said tissue slice;
   (b) preparing a dilution range of said at least one target molecule, said preparing of said dilution range comprising:
      (i) preparing a tissue homogenate of a tissue identical to the tissue of step (a);
      (ii) adding a first known concentration of said at least one target molecule to a sample of said tissue homogenate prepared in step (i);
      (iii) adding a second known concentration of said at least one target molecule to a sample of said tissue homogenate prepared in step (i), said second known concentration of said at least one target molecule differing from the first known concentration of said at least one target molecule;
      (iv) optionally repeating steps (ii) and (iii) with at least one additional sample of tissue homogenate from step (i) and at least one additional known concentration of said at least one target molecule that differs from said first and said second concentration of said target molecule;
      (v) solidifying the samples of tissue homogenates containing said known concentrations of said at least one target molecule;
      (vi) slicing with substantially identical thickness said solidified samples of tissue homogenates containing different known concentrations of said at least one target molecule; and
      (vii) performing mass spectrometry analysis on said sliced solidified samples of tissue homogenates and detecting a signal representative of each concentration of said at least one target molecule in each tissue homogenate slice and quantifying said target molecule in said tissue slice; and
   (c) determining the quantity of target molecule in the tissue by using the dilution range prepared in step (b).

* * * * *